United States Patent

Waterfield et al.

[11] Patent Number: 6,022,528
[45] Date of Patent: Feb. 8, 2000

[54] ORAL COMPOSITIONS

[75] Inventors: Philip Christopher Waterfield; Richard Huw Davies, both of Bebington Wirral, United Kingdom; Frederique Villiard, Paris, France

[73] Assignee: Chesebrough-Pond's USA Co., Greenwich, Conn.

[21] Appl. No.: 09/141,254

[22] Filed: Aug. 27, 1998

[30] Foreign Application Priority Data

Sep. 2, 1997 [EP] European Pat. Off. ............... 97306736

[51] Int. Cl.[7] ............... A61K 7/16; A61K 7/18; A61K 7/20; A61K 9/46
[52] U.S. Cl. ............... 424/49; 424/44; 424/52; 424/53; 424/55
[58] Field of Search .......................... 424/49–58

[56] References Cited

U.S. PATENT DOCUMENTS

| | | | |
|---|---|---|---|
| 3,629,468 | 12/1971 | Andersen | 424/44 |
| 3,729,553 | 4/1973 | Gold et al. | 424/44 |
| 3,888,976 | 6/1975 | Mikvy | 424/44 |
| 3,962,417 | 6/1976 | Howell | 424/44 |
| 4,098,435 | 7/1978 | Weyn . | |
| 4,127,645 | 11/1978 | Witzol | 424/44 |
| 4,150,113 | 4/1979 | Hoogendoorn et al. | 424/50 |
| 4,178,362 | 12/1979 | Hoogendorn et al. | 424/50 |
| 4,487,757 | 12/1984 | Kiozpeoplou | 424/44 |
| 4,687,663 | 8/1987 | Schaefer | 424/53 |
| 5,616,313 | 4/1997 | Williams et al. . | |
| 5,804,165 | 9/1998 | Arnold | 424/44 |
| 5,817,294 | 10/1998 | Arnold | 424/44 |
| 5,855,871 | 1/1999 | Masters et al. | 424/44 |

FOREIGN PATENT DOCUMENTS

| | | |
|---|---|---|
| 2 361 851 | 8/1977 | France . |
| 1492660 | 5/1977 | United Kingdom . |
| 2 112 642 | 7/1983 | United Kingdom . |
| 8810110 | 1/1988 | WIPO . |
| 92/04007 | 3/1992 | WIPO . |
| 92 07550 | 5/1992 | WIPO . |
| 95/02392 | 1/1995 | WIPO . |
| 9502392 A1 | 1/1995 | WIPO . |
| 95 12380 | 5/1995 | WIPO . |
| 96 19189 A2 | 6/1996 | WIPO . |
| 96/19189 | 6/1996 | WIPO . |
| 9843603 A1 | 1/1998 | WIPO . |
| 98/43603 | 8/1998 | WIPO . |

OTHER PUBLICATIONS

West Textbook of Biochemistry 4th Ed MacMillan NY pp. 494–497 "Acidity of Saliva" (pH 5.73–7.05, 6.1–6.5 6.75 aver.), Jan. 1966.

*Primary Examiner*—Shep K. Rose
*Attorney, Agent, or Firm*—Milton L. Honig

[57] ABSTRACT

The present invention relates to an effervescent oral care composition with improved interproximal delivery properties. The composition comprises a first composition with about 2.5% by weight of an alkalimetal bicarbonate and a second composition with an acidic compound. Upon bringing the two compositions into contact with each other, e.g. by extruding them from a multicompartment container through a single outlet orifice, the alkalimetal bicarbonate and the acidic compound react with each other, causing an effervescent effect. By using 0.02% to less than 0.5% by weight, calculated on the total weight of the oral care composition, of the acidic compound, the interproximal delivery properties of the composition are significantly improved.

7 Claims, No Drawings

ORAL COMPOSITIONS

BACKGROUND OF THE INVENTION

1. Field of the Invention

The present invention relates to oral compositions which contain ingredients which upon contact with each other will produce an effervescent effect.

2. The Related Art

More particularly, the present invention relates to oral compositions which consist of a first composition containing one of the ingredients necessary to produce an effervescent effect, and a second composition containing the other ingredient necessary to produce the effervescent effect.

Oral products consisting of a first composition and a second composition, each composition containing separated reactive components which, when brought together develop effervescence are already known in the art. Thus, in GB-A-2,112,642 (Colgate), a dual-compartment dentifrice dispensing container is described which contains in one compartment a portion of the dentifrice containing as reactive component sodium bicarbonate, and in the other compartment another portion of the dentifrice containing as reactive component an acidic compound.

Upon dispensing the two dentifrice portions from the container through a single outlet orifice, the two portions are brought into intimate contact, and the sodium bicarbonate and acidic compound react with each other, thereby releasing carbon dioxide gas which causes the dentifrice to effervesce when used in the mouth.

The first portion of this dentifrice, that is the portion containing the sodium bicarbonate, contains at least about 15% by weight of sodium bicarbonate, and preferably from 20–40% by weight.

One of the drawbacks of sodium bicarbonate is its salty taste, and this is acknowledged in the above GB-A-2,112, 642. Formulations according to this patent are stated to have an initial salty taste, which changed to a pleasingly sweeter flavour during brushing, caused by the effervescence.

According to WO-A-95/02392 (Unilever), lowering the sodium bicarbonate level resulted in a significantly less salty taste, without any significant reduction of effervescence. This provided for a dentifrice with an improved consumer acceptability in that it combined the required effervescence with a significantly more pleasant, less salty taste.

In WO-A-96/19189 (Lingner & Fischer) similar compositions are described. It is stated in this prior proposal that during the cleaning procedure all the regions of the surface of the teeth are contacted uniformly by these compositions. The distribution of the active ingredient obtainable during the teeth cleaning procedure is stated to be optimised, due to the intensive formation of foam.

The level of the acidic compound, used in the formulations according to the above prior proposals, generally range from 1–20% by weight of the composition comprising the acidic compound, preferably 3–10% by weight. Since the composition comprising the bicarbonate and the composition comprising the acidic compound are usually and advantageously combined with each other in a volumetric ratio of 1:1, the lower level of the acidic compound, calculated on the total oral care composition is about 0.5% by weight, depending upon the densities of the first and second composition of the oral care product.

SUMMARY OF THE INVENTION

We have now surprisingly found, that substantially lowering the level of the acidic compound in the second composition of the above-type of oral care products results in a significantly improved delivery of active ingredients by the oral care product to the interproximal spaces between and to the surfaces of the teeth, during cleaning of the teeth. Despite this lowering of the level of the acidic compound, the oral care product of the invention still produces an effervescent effect upon use, and tastes better than the products according to the prior proposals.

We have found that lowering the level of the acid compound to even as low as 0.02% by weight (calculated on the total product) produces the above surprising benefits concerning improved delivery, effervescence and taste. The upper level of the acidic compound should be below 0.5% to still obtain the benefits of the invention, and it has been found that optimal results are obtained with a level of acidic compound ranging from 0.025%–0.4%, particularly 0.03–0.3% by weight, all calculated on the total oral care product.

Consequently, in its broadest aspect the present invention relates to an oral care composition comprising a first composition which contains as essential ingredient an alkalimetal bicarbonate in an amount of about 2.5—about 10% by weight of the first composition, and a second composition which contains as essential ingredient an acidic compound, and is characterised in that the acidic compound is present in the second composition in an amount of 0.02% to less than 0.5% by weight, calculated on the weight of the total oral care composition.

DETAILED DESCRIPTION OF THE INVENTION

The first composition contains from about 2.5—about 10% by weight, preferably from 3–10% by weight of the alkalimetal bicarbonate. The alkalimetal bicarbonate can be sodium or potassium bicarbonate, or a mixture thereof. Alkalimetal sesquicarbonate can also be used. Preferred is sodium bicarbonate.

The first composition can be formulated into any convenient form, such as a paste or a gel or a liquid. A preferred form is a paste. The paste is usually formulated to have a pH of between 8.0 and 10.0, preferably 8.5–9.5. This paste may contain other, conventional toothpaste ingredients provided they are compatible with the alkalimetal bicarbonate. Thus, the paste will usually contain an abrasive cleaning agent such as chalk, silicas, hydroxyapatites, dicalciumphosphate, calcium pyrophosphates, metaphosphates and so on, usually in amounts between 5 and 60% by weight.

Furthermore, the paste may contain humectants such as glycerol, sorbitol, propyleneglycol, polyethyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Bicarbonate-compatible flavours such as peppermint and spearmint oils may also be included, as well as preservatives, colouring agents, pH-adjusting agents, sweetening agents and so on.

Anti-bacterial active agents such as Triclosan may also be included, as well as anti-caries active agents such as sodium monofluorophosphate, sodium fluoride, sodium trimetaphosphate, calcium glycerophosphate, calcium lactate etc.

Furthermore, anticalculus active agents such as alkalimetal pyrophosphates may be included, as well as other condensed phosphates. Alkalimetal silicates may also be included as a processing aid.

Further optional active ingredients are Vitamin E, enzymes, antibodies, bacteriocins, statherins, defensins, bacteriophages, casein and casein digests, antimicrobial peptides, enzyme inhibitors, antibacterial adhesion polymers, lectins, tissue respiratory factor.

The present invention is particularly useful for oral care products containing an anti-bacterial agent and/or an anti-caries agent to provide for improved delivery to the interproximal spaces between the teeth of the anti-bacterial and or anti-caries agent upon use of the oral care products.

Anionic, nonionic, zwitterionic and ampholytic surfactants may also be included, such as sodium laurylsulphate, cocamidopropylbetain and ethylene oxide/propylene oxide block copolymers, as well as lactobionamides and glycoside derived surfactants.

The second composition which contains the acidic compound can also be formulated in any suitable form, such as a paste, a liquid or a gel. The gel form is preferred. It is usually formulated to a pH of between 1.0 and 5.5, preferably 1.5–4.5.

Suitable examples of acidic compounds which can be used in the present invention are organic and/or inorganic acids such as organoleptically acceptable acids such as malic acid, glycolic acid, adipic acid, tartronic acid, phosphocitric acid, glycerophosphoric acid, citric acid, succinic acid, tartaric acid, lactic acid fruit extracts containing α-hydroxy acids, phosphoric acid, pyrophosphoric acid, boric acid and so on. Fruit extracts containing mixtures of α-hydroxy acid such as glycolic, lactic and malic acid, in admixture with citric acid are preferred. Acid anhydrides may also be used, e.g. citric acid anhydride. Acid salts of the above acids may also be used, such as mono- and dihydrogen alkalimetal orthophosphate, mono-, di-, and trihydrogen alkalimetal pyrophosphate, mono- and di-alkalimetal citrates.

In general, as said above the amount of acid compound in the second composition ranges from 0.02%-less than 0.5%, usually 0.025–0.4% and preferably from 0.03–0.3%. Naturally, the amount of acid compound should be correlated with the amount of bicarbonate in the first composition to provide the required effervescence. Usually, the amount of bicarbonate in the first composition to the amount of acid compound in the second composition will have a weight ratio of 500:1 to up to 5:1. Preferred ratios range from 250:1 to 125:1.

The second composition may, furthermore, comprise further optional active ingredients such as peroxides such as hydrogen peroxide, anticaries agents such as sodium fluoride and sodium monofluorophosphate, stannous compounds such as stannous fluoride and stannous pyrophosphate, zinc compounds such as zinc citrate and zinc sulphate, spangolites and spangolite-like materials, zinc hydroxyapatites, zinc hydrotalcites and zinc hydrotalcite-like materials, zinc silicates, zinc-containing zeolites, copper compounds such as copper sulphate, silver compounds such as silver-containing zeolites, Triclosan, chlorhexidine, potassium chloride, potassium acetate, potassium nitrate, potassium citrate, potassium hydrogen citrate, strontium chloride, strontium acetate, strontium citrate, vitamin E, gelling agents such as xanthan gum, CMC, polyacrylates, carboxyvinyl polymers, surfactants such as anionic, cationic, nonionic, zwitterionic and ampholytic surfactants, humectants such as sorbitol, glycerol, xylitol, propyleneglycol, polyethylene glycol, abrasives cleaning agents such as silica, etc.

The first and second composition may be separately packed in individual suitable containers, from which the consumer can extrude suitable amounts just before mixing it onto the brush or in the mouth.

The compositions are, however, preferably packed separately in multicompartment containers from which the compositions can be extruded through a single orifice to facilitate the use by the consumer. Suitable examples of multicompartment containers are given in U.S. Pat. Nos. 5,038,963, 5,020,694, 4,964,539, 4,528,180 and 4,849,213.

Naturally, the composition of each formulation in such multicompartment container, as well as the amount of each composition in the compartments of the container should be correlated, so that upon extrusion the properly balanced amounts of each composition is extruded to provide the required effervescence.

The invention will further be illustrated by way of Example.

EXAMPLE 1

The following formulation was prepared and packed in a dual compartment piston-type dispenser as described in U.S. Pat. No. 5,020,694.

| First Position (paste) | % by Weight | Second Composition (gel) | % by Weight |
|---|---|---|---|
| Sorbitol (70%) | 35.00 | Sorbitol (70%) | 40.00 |
| Sodium saccharin | 0.30 | Sodium saccharin | 0.20 |
| titanium dioxide | 0.50 | colour | 0.005 |
| polyethylene glycol (MW 1500) | 5.00 | grapefruit extract (containing | 0.5 |
| sodium monofluorophosphate | 1.18 | citric acid, glycolic acid, lactic | |
| abrasive silica | 15.00 | acid and malic acid | |
| thickening silica | 3.00 | in propylene glycol) | |
| sodium carboxymethyl-cellulose | 0.70 | Zinc sulphate heptahydrate | 1.00 |
| sodium bicarbonate | 9.00 | Sodium monofluorophosphate | 1.18 |
| sodium laurylsulphate | 3.00 | ethylene oxide/ propylene oxide | 22.00 |
| Triclosan | 0.60 | block copolymer | |
| flavour | 1.00 | (Poloxamer 407) | |
| water | 9.5 | flavour water | |

This product had a better taste, and improved interproximal delivery properties, compared with a product with much higher levels of acidic compound in the second composition.

EXAMPLE 2

Another formulation according to the present invention is:

| First Composition (paste) | % by Weight | Second Composition (gel) | % by Weight |
|---|---|---|---|
| Glycerol | 40.00 | Glycerol | 35.00 |
| Sodium saccharin | 0.3 | Sodium saccharin | 0.30 |
| titanium dioxide | 0.5 | colour agent | 0.005 |
| polyethylene glycol (MW 1500) | 5.00 | apple extract (containing | 0.1 |
| sodium fluoride | 0.32 | citric acid, glycolic | |
| abrasive silica | 8.00 | acid, lactic acid and | |
| thickening silica | 6.00 | malic in propylene | |
| sodium | 0.6 | glycol | |

-continued

| First Composition (paste) | % by Weight | Second Composition (gel) | % by Weight |
|---|---|---|---|
| carboxymethyl-cellulose | | Zinc sulphate heptahydrate | 1.00 |
| sodium bicarbonate | 8.00 | Sodium fluoride | 0.32 |
| sodium laurylsulphate | 2.00 | Sodium laurylsulphate | 1.00 |
| | | Poloxamer 407 | 20.00 |
| Triclosan | 0.5 | flavour | 1.00 |
| flavour | 1.00 | water | 9.5 |
| water | 9.5 | | |

This formulation has a better taste and improved interproximal delivery properties than similar products with a much higher level of acidic compound.

We claim:

1. An effervescent oral care composition, comprising a first gel, liquid or paste composition with a pH of between 8.0 and 10.0 containing as an essential ingredient from about 2.5% to about 10% by weight ot an alkalimetal bicarbonate, and a second gel, liquid or paste composition having pH between 1.0 and 5.5 containing as essential ingredient an acidic compound, characterized in that the acidic compound is present in the second composition in an amount of 0.02% to less than 0.5% by weight, calculated on the weight of the total oral care composition, said composition not relying on acidic saliva to generate carbon dioxide effervescence with said bicarbonate, tasting better, and with improved interproximal delivery properties as compared to the same composition with a higher level of acid compound.

2. A composition according to claim 1, characterized in that the acidic compound in the second composition is present in an amount of 0.025%–0.4% by weight, calculated on the weight of the total oral care composition.

3. A composition according to claim 1, characterised in that the acidic compound is present in an amount of 0.03–0.3% by weight, calculated on the weight of the total oral care composition.

4. A composition according to claim 1, characterised in that the acidic compound comprises an α-hydroxy acid.

5. A composition according to claim 4, characterised in that the -hydroxy acid is or comprises lactic acid, glycolic acid, and/or malic acid.

6. A composition according to claim 1, characterised in that the acidic compound is a fruit extract.

7. A composition according to claim 1, characterised in that the first and the second composition are separately packed in a multicompartment container having a single outlet orifice.

* * * * *

UNITED STATES PATENT AND TRADEMARK OFFICE
CERTIFICATE OF CORRECTION

PATENT NO. : 6,022,528
DATED : February 8, 2000
INVENTOR(S) : Waterfield et al.

It is certified that error appears in the above-indentified patent and that said Letters Patent is hereby corrected as shown below:

Assignee Section change "Chesebrough-Pond's USA Co.," to
-- Chesebrough-Pond's USA Co., Division of Conopco, Inc. -- ;

Column 5, line 21 change "ot" to -- of -- ; and

Column 6, line 17 change " -hydroxy" to -- α-hydroxy -- .

Signed and Sealed this

Twenty-fourth Day of April, 2001

Attest:

NICHOLAS P. GODICI

Attesting Officer

Acting Director of the United States Patent and Trademark Office